United States Patent [19]

Jonas et al.

[11] 3,989,833
[45] Nov. 2, 1976

[54] PHARMACEUTICAL COMPOSITIONS CONTAINING ADENINE DERIVATIVES

[75] Inventors: Rochus Jonas; Werner Mehrhof; Karl Heinz Becker; Hans-Jochen Schliep, all of Darmstadt, Germany

[73] Assignee: Merck Patent Gesellschaft mit beschrankter Haftung, Darmstadt, Germany

[22] Filed: Nov. 4, 1974

[21] Appl. No.: 520,888

[30] Foreign Application Priority Data
Nov. 7, 1973 Germany............................ 2355536

[52] U.S. Cl. .................................................. 424/253
[51] Int. Cl.² ........................................... A61K 31/52
[58] Field of Search ..................................... 424/253

[56] References Cited
UNITED STATES PATENTS
3,838,147  9/1974  Pohlke ............................. 424/180

Primary Examiner—Jerome D. Goldberg
Attorney, Agent, or Firm—Millen, Raptes & White

[57] ABSTRACT

Adenine derivatives of the formula

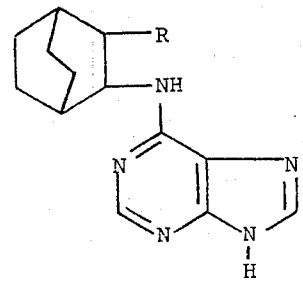

wherein R is phenyl or thienyl, and the physiologically acceptable acid addition salts thereof, possess, with good compatibility, cardio-active properties and are produced by the reaction of a purine derivative of the formula

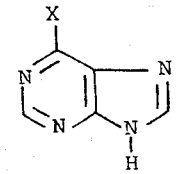

wherein X is F, Cl, Br, I, $SR_1$, $SOR_1$, $SO_2R_1$ or $OSi(CH_3)_3$, $R_1$ being alkyl of 1–4 carbon atoms, phenyl or benzyl, with an amine of the formula

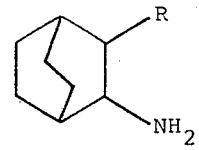

wherein R has the values given above, or a salt thereof.

7 Claims, No Drawings

PHARMACEUTICAL COMPOSITIONS CONTAINING ADENINE DERIVATIVES

BACKGROUND OF THE INVENTION

This invention relates to the novel adenine derivatives.

Surprisingly, the adenine derivatives of this invention have advantageous therapeutic properties similar to the corresponding adenosine derivatives of German Unexamined Laid-Open Applications DOS 2,117,577 and DOS 2,205,002 (U.S. application Ser. No. 242,741, filed Apr. 10, 1972). From the disclosures of these applications, a class of compounds embracing the novel compounds of this invention are known to be useful as intermediates for the production of these adenosines.

SUMMARY OF THE INVENTION

In a composition aspect, this invention relates to novel adenine derivatives of general Formula 1

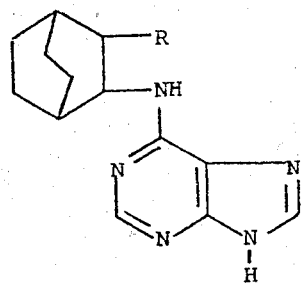

1 wherein R is phenyl or thienyl, and the physiologically acceptable acid addition salts thereof.

In another composition aspect, this invention relates to pharmaceutical compositions comprising the novel adenosine derivatives.

In a process aspect, this invention relates to processes for the production of the novel adenosine derivatives and to their use.

DETAILED DISCUSSION

Compared to the above-discussed known adenosines, the novel adenosine derivatives of this invention have significantly better acute compatibility as compared to these sugar-moiety-containing compounds, the acute compatibility being by more than tenfold greater, for example, in case of the thienyl-2 compound. This results in an essentially more favorable span of the therapeutic spectrum than in case of the corresponding adenosine derivatives. The compatibility was determined by measuring the vomit threshold in dogs and cats, as well as by examination of the heart-lung preparation (isolated organs, guinea pigs) for EKG changes.

More specifically, the compounds of Formula 1 and the physiologically acceptable acid addition salts thereof increase the coronary circulation or raise the partial oxygen pressure in the coronary-venous blood (in dogs) or both. In particular, these compounds have the advantage of being effective in an intravasal pain pattern (in dogs). This activity is of significance in the treatment of the pain conditions occurring in angina pectoris. Also, the arrhythmia induced in rats by the administration of potassium is extensively overcome (depending on the dosage) by an oral application of the compounds. The novel compounds have other activities which are effective on the circulation, inhibit the lipolysis and/or lower the cholesterol level.

The compounds can accordingly be employed as medicinal agents and also as intermediates for the preparation of other medicines, for example as intermediates for the production of the aforementioned adenosine derivatives by reaction with ribose and ribose derivatives, respectively, e.g., as disclosed in Ser. No. 242,741.

In its process aspect, this invention relates to a process for the preparation of the novel compounds of this invention, which comprises a. reacting a purine derivative of general Formula 2

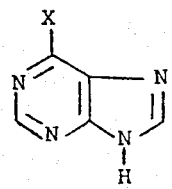

2 wherein X is F, Cl, Br, I, $SR_1$, $SOR_1$, $SO_2R_1$ or $OSi(CH_3)_3$ and $R_1$ is alkyl of 1–4 carbon atoms, phenyl or benzyl, with an amine of the general Formula 3

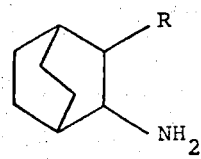

3 wherein R has the values given above, or with a salt thereof; or b. reacting a pyrimidine derivative of the general Formula 4

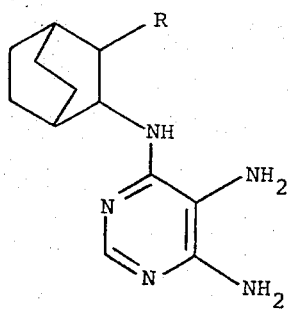

4 wherein R has the values given above with an orthoformic acid ester in the presence of a carboxylic acid anhydride; or c. treating a compound otherwise corresponding to general Formula 1 but bearing in place of at least one hydrogen atom at least one group which can be split off by solvolysis or hydrogenolysis with a solvolytically or hydrogenolytically active agent; and optionally thereafter converting a thus-obtained base of the general Formula 1 by treatment with an acid into a physiologically acceptable acid addition salt thereof or liberating a compound of general Formula 1 from a salt thereof by treatment with a base.

All of these reactions are conducted according to methods known per se from the literature.

In Formula 2, X preferably is Cl or Br but can also be, for example, F, I, methylmercapto, ethylmercapto, phenylmercapto, benzylmercapto, methylsulfinyl, ethylsulfinyl, methylsulfonyl, ethylsulfonyl or trimethylsilyloxy. $R_1$ preferably is methyl or ethyl.

The reaction of the purine derivatives 2, especially the 6-chloropurine, with the amines 3 is preferably effected in the presence of an inert solvent. Suitable solvents are alcohols, e.g., methanol, ethanol and preferably isopropanol; ethers, e.g., tetrahydrofuran and dioxane; and amides, e.g., dimethylformamide. In the reaction, it is advantageous to add an organic or inorganic base, e.g., triethylamine, pyridine or potassium carbonate. The reaction temperatures range between about 0° and about 180°, preferably at the boiling point of the solvent employed. The reaction times are usually between about 0.5 and about 30 hours, preferably about 1 to 5 hours. The reaction can also be conducted in the melt in the absence of a solvent at temperatures of between about 70° and about 180°, in which case, the reaction times range from about 3 minutes to about 5 hours.

The adenine derivatives 1 are also obtainable by reacting the pyrimidine derivatives 4 with orthoformic acid esters, e.g., with trimethyl or tripropyl orthoformate, but preferably with triethyl orthoformate. A preferred carboxylic acid anhydride is acetic anhydride, and furthermore also, for example, propionic acid anhydride or butyric acid anhydride. The ratio of ortho ester to anhydride is suitably from 10:1 to 1:1. The condensation is effected at temperatures of between about 0° and about 150°, preferably at the boiling point of the reaction mixture. The reaction time ranges between about 0.1 and 10 hours, preferably 0.5 to 3 hours.

The adenine derivatives 1 are also obtainable by solvolysis or hydrogenolysis of preliminary products which otherwise correspond to Formula 1. Preferably, the corresponding adenosine derivatives are utilized in this variation of the process, which otherwise correspond to Formula 1 but bear an additional ribose group in the 9-position of the purine system. Other suitable starting compounds are, for example, those otherwise corresponding to Formula 1, but containing in the 2- and/or 8-position of the purine system additionally one (or two) Cl, Br, I, $SR_1$, $SOR_1$ or $SO_2R_1$ groups and/or in the 9-position a benzyl group or a ribose residue, the OH groups of which are present in the functionally modified form, e.g., as benzyl ether or as acetoxy groups.

The ribose group is preferably split off from the adenosine derivatives with the aid of an acid, preferably a mineral acid, such as hydrochloric acid or sulfuric acid, a strong organic acid, e.g., p-toluenesulfonic acid, or a Lewis acid, e.g., boron trifluoride. Suitably, an inert solvent is added, e.g., methanol, ethanol, propanol, tetrahydrofuran, dimethylformamide, or water, or mixtures of the aforementioned solvents or of an organic solvent with an aqueous acid. Preferably, the reaction is conducted in a mixture of equal amounts of ethanol and 12% strength aqueous hydrochloric acid. By this method, the compounds 1 are obtained after the working-up operation in the form of their readily crystallizing hydrochlorides. The reaction temperature ranges from about 0° to about 100°, preferably the boiling temperature of the solvent used. The reaction times are from about 0.1 to about 10 hours, preferably 0.1 to 2 hours.

The solvolysis can also be effected in one of the above-indicated solvents and/or in a solvent mixture under the influence of a base, for example, metal alcoholates (e.g., sodium ethylate), sodium hydroxide solution or potassium hydroxide solution. Preferably, potassium tert.-butylate is utilized, e.g., in a mixture of dioxane and tert.-butanol, at temperatures of about 0° to about 100°, preferably 10° to 40°. The reaction times are, in this process, about 1 hour to about 5 days.

The solvolysis of the remaining, above-mentioned preliminary products takes place in a similar manner. Benzyl groups and/or halogen atoms can also be removed by hydrogenolysis, e.g., with hydrogen on a noble metal catalyst, such as Pd, in one of the aforementioned solvents.

The free adenine bases of Formula 1 show relatively unsharp melting points. They are, therefore, characterized suitably in the form of their acid addition salts, obtainable from the free bases with acids in the usual manner. Advantageous for this reaction are, in particular, those acids yielding physiologically acceptable salts. Preferably, inorganic or strong organic acids can be utilized, for example sulfuric acid, nitric acid, hydrohalic acids, such as hydrochloric acid or hydrobromic acid, phosphoric acids, such as orthophosphoric acid, aliphatic, alicyclic, araliphatic, aromatic and heterocyclic mono- or polybasic sulfonic acids, e.g., methane- and ethanesulfonic acid, ethanedisulfonic acid, 2-hydroxy-ethanesulfonic acid, benzenesulfonic acid, p-toluenesulfonic acid, naphthalene-mono- and -disulfonic acids. The free bases of Formula 1 can, if desired, be liberated from the salts thereof by treatment with a strong base, e.g., sodium or potassium hydroxide and sodium or potassium carbonate.

The compounds of Formula 1 contain two centers of asymmetry and are ordinarily present in the racemic form. They can be obtained during the synthesis as mixtures of racemates, from which the individual racemates can be isolated, for example, by repeated recrystallization from suitable solvents and can thus be obtained in pure form. However, usually only a single, uniform racemate is produced during the synthesis.

The thus-obtained racemates can be separated mechanically or chemically into the optical antipodes thereof in accordance with conventional methods.

It is also possible to obtain optically active compounds in accordance with the above-described methods using starting materials which are optically active.

The novel compounds of Formula 1 and/or the physiologically acceptable acid addition salts thereof can be utilized in a mixture with solid, liquid and/or semiliquid excipients as medicinal agents in the human or veterinary medicine. Suitable vehicles are those organic or inorganic substances which are suitable for parenteral, enteral, or topical application and which do not react with the novel compounds, such as, for example, water, vegetable oils, polyethylene glycols, gelatin, lactose, amylose, magnesium stearate, talc, vaseline, cholesterol. Suitable for parenteral application are, in particular, solutions preferably oily or aqueous solutions, as well as suspensions, emulsions or implants. Suitable for enteral administration are tablets, dragees, capsules, syrups, elixirs or suppositories, and for topical application ointments, creams or powders. The above-mentioned preparations can optionally be sterilized or combined with auxiliary agents, such as preservatives, stabilizers or wetting agents, salts for influencing the osmotic pressure, buffers, coloring, flavoring and/or aromatic substances.

The compounds of this invention are administered to animals upon oral application preferably in doses of about 0.05 to 200 mg. per kg. of body weight, especially 0.1 to 20 mg. per kg. of body weight. In humans, the doses are normally somewhat lower, generally from 3 to 500 mg. per dosage unit is administered.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The temperatures herein are set forth in degrees Celsius.

EXAMPLE 1

4.1 g. of 6-chloropurine and 6.5 g. of [3-(thienyl-3)-bicyclo[2,2,2]octyl-2]-amine are dissolved in 100 ml. of isopropanol and, after the addition of 15 ml. of triethylamine, refluxed for 6 hours. The residue obtained after concentration is taken up in 100 ml. of ethyl acetate, the solution is extracted with 1% acetic acid and water, and dried. The reaction product is concentrated by evaporation, thus obtaining N(6)-[3-(thienyl-3)-bicyclo[2,2,2]octyl-2]-adenine, m.p. 139°–144°.

Analogously, the remaining compounds of Formula 1 are obtained from 6-chloropurine and [3-phenylbicyclo[2,2,2]octyl-2]-amine and [3-(thienyl-2)-bicyclo[2,2,2]octyl-2]-amine, respectively.

EXAMPLE 2

7.2 g. of 4,5-diamino-6-[3-phenylbicyclo[2,2,2]octyl-2-amino]-pyrimidine is refluxed in a mixture of 33 ml. of triethyl orthoformate and 33 ml. of acetic anhydride for 2 hours and then concentrated by evaporation. The residue is combined with 35 ml. of ethanol and 70 ml. of 2N sodium hydroxide solution and heated for 20 minutes to 40°. Thereafter, the alcohol is distilled off, and the remaining solution is neutralized with acetic acid. The thus-precipitated adenine base is filtered and, to convert same into the hydrochloride, evaporated with 50 ml. of 2N hydrochloric acid. The thus-produced N(6)-[3-phenylbicyclo[2,2,2]octyl-2]-adenine is filtered, washed with water and then with acetone; m.p. 247°–248°.

Analogously, the remaining compounds of Formula 1 are obtained from 4,5-diamino-6-[3-(thienyl-2)-bicyclo[2,2,2]octyl-2-amino]-pyrimidine and 4,5-diamino-6-[3-(thienyl-3)-bicyclo[2,2,2]-octyl-2-amino]-pyrimidine, respectively.

EXAMPLE 3

8 g. of N(6)-[3-(thienyl-2)-bicyclo[2,2,2]octyl-2]-adenosine is refluxed with 150 ml. of ethanol and 150 ml. of 12% aqueous hydrochloric acid for 1 hour. The alcohol is then removed by distillation, and the solution is cooled. The thus-precipitated sediment is vacuum-filtered and washed first with water and then with acetone, thus producing N(6)-[3-(thienyl-2)-bicyclo[2,2,2]-octyl-2]-adenine monohydrochloride, m.p. 257°.

Analogously, the remaining compounds of Formula 1 are obtained by hydrolysis of N(6)-[3-phenylbicyclo[2,2,2]octyl-2]-adenosine and of N(6)-[3-(thienyl-3)-bicyclo[2,2,2]octyl-2]-adenosine, respectively.

The following examples relate to pharmaceutical preparations containing adenines of general Formula 1:

EXAMPLE A: Tablets

A mixture consisting of 20 kg. of N(6)-[3-(thienyl-2)-bicyclo[2,2,2]octyl-2]-adenine monohydrochloride, 500 kg. of lactose, 160 kg. of corn starch, 20 kg. of cellulose powder, and 20 kg. of magnesium stearate is compressed to tablets in the usual manner, so that each tablet contains 20 mg. of the active agent.

EXAMPLE B: Dragees

Tablets are compressed analogously to Example A and are thereafter coated in the usual way with a coating consisting of sugar, corn starch, talc, and tragacanth.

Analogously, tablets and dragees can be prepared which contain one or more of the other effective agents of Formula 1 and/or the physiologically acceptable acid addition salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition adapted for oral administration in the form of tablets, dragees, capsules, a syrup or an elixir and comprising, in admixture with a pharmaceutically acceptable carrier, from 3 to 500 mg. per unit dosage of an adenine derivative of the formula

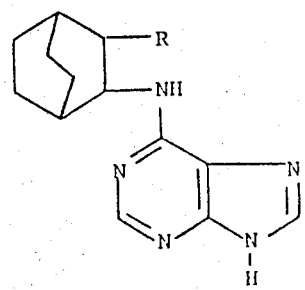

wherein R is phenyl or thienyl, or a physiologically acceptable acid addition salt thereof.

2. A composition of claim 1, wherein the adenine derivative N(6)-[3-(thienyl-2)-bicyclo[2,2,2]octyl-2]-adenine.

3. A composition of claim 1, wherein the adenine derivative N(6)-[3-(thienyl-3)-bicyclo[2,2,2]octyl-2]-adenine.

4. A composition of claim 1, wherein the adenine derivative N(6)-[3-phenylbicyclo[2,2,2]octyl-2]-adenine.

5. A composition of claim 1 in the form of dragees.

6. A composition of claim 1 in tablet form.

7. A method for the treatment of intravascular pain in humans which comprises administering to a human suffering therefrom an amount from 3 to 500 mg. per dosage of an adenine derivative of the formula

wherein R is phenyl or thienyl, or a physiologically acceptable acid addition salt thereof effective to ameliorate the pain.

* * * * *